United States Patent [19]
Beger

[11] Patent Number: 6,021,694
[45] Date of Patent: Feb. 8, 2000

[54] SURGICAL TORQUE WRENCH

[75] Inventor: Jens Beger, Tuttlingen, Germany

[73] Assignee: Aseculap AG & Co. KG, Tuttlingen, Germany

[21] Appl. No.: 09/173,997

[22] Filed: Oct. 16, 1998

Related U.S. Application Data

[63] Continuation of application No. PCT/EP97/01312, Mar. 15, 1997.

[30] Foreign Application Priority Data

Apr. 18, 1996 [DE] Germany ............ 196 15 241

[51] Int. Cl.$^7$ ............................. B25B 23/159
[52] U.S. Cl. .................... 81/483; 73/862.21
[58] Field of Search ............ 87/478, 483; 74/527; 73/862.21, 862.22, 862.26

[56] References Cited

U.S. PATENT DOCUMENTS

| | | | |
|---|---|---|---|
| 2,959,078 | 11/1960 | Skidmore | 81/483 |
| 4,655,104 | 4/1987 | Blattner | 81/483 |
| 4,870,879 | 10/1989 | Shieh | 81/483 |
| 5,337,638 | 8/1994 | Coss et al. | |
| 5,503,042 | 4/1996 | Larson et al. | 81/483 X |
| 5,507,211 | 4/1996 | Wagner | |

FOREIGN PATENT DOCUMENTS

| | | | |
|---|---|---|---|
| 0 704 281 | 4/1996 | European Pat. Off. | |
| 1063803 | 12/1953 | France | 81/483 |
| 87 05 205 | 8/1987 | Germany | |
| 41 29 025 | 3/1993 | Germany | |
| 732013 | 6/1955 | United Kingdom | 81/483 |

*Primary Examiner*—James G. Smith
*Attorney, Agent, or Firm*—Barry R. Lipsitz; Ralph F. Hoppin

[57] ABSTRACT

A surgical torque wrench having jaws for application to a rotating part and a handle removably secured to the jaws. The jaws and handle are secured together about a pivot that is parallel to the axis of rotation of the rotating part. A securing device is fitted between the jaws and the handle which secures them relative to each other in a given angular position and is releasable when a given torque is reached. A removable handle member is provided to fix the jaws to the handle to allow for application of torque.

41 Claims, 5 Drawing Sheets

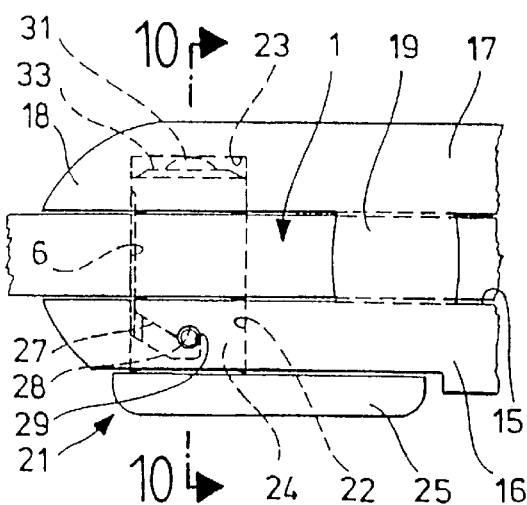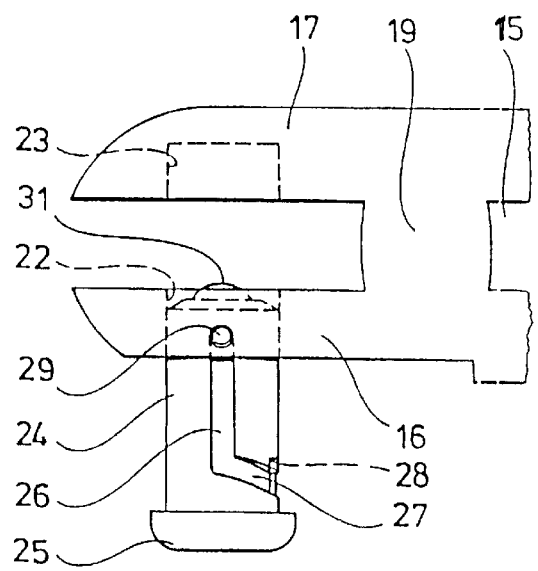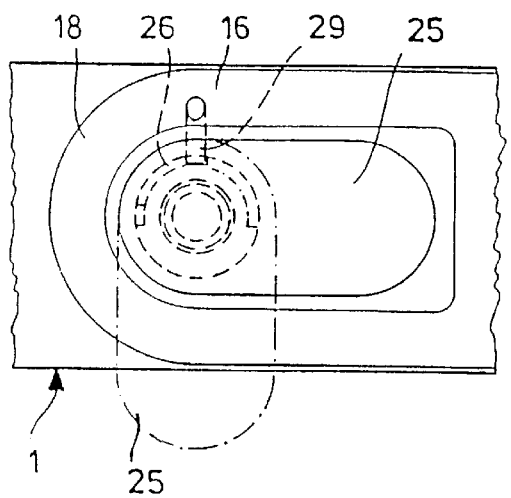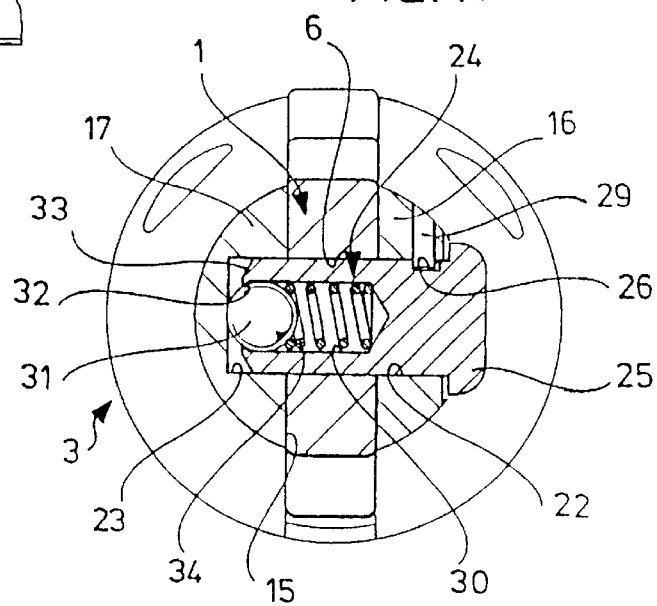

SURGICAL TORQUE WRENCH

The present disclosure is a continuation of International Application PCT/EP97/01312 of Mar. 15, 1997, the entire specification of which is incorporated herein by reference.

BACKGROUND OF THE INVENTION

The invention relates to a surgical torque wrench having a jaw part for application to an element to be turned and adjoining the jaw part a handle part for turning the jaw part, wherein the jaw part and the handle part are joined to one another for pivotal movement about a pivot axis extending parallel to the axis of rotation of the element to be turned, wherein there is provided between jaw part and handle part a holding device which fixes jaw part and handle part in a certain angular position relative to one another and which is releasable when a certain torque is exceeded, and wherein there is operative between jaw part and handle part a stop which limits the pivot angle of the jaw part relative to the handle part when the holding device is released.

Such torque wrenches are used to screw in or release screws or nuts, for example, in orthopedic implants or endoprostheses.

It is desirable to be able to apply precisely determinable maximum torques to the elements to be turned with the torque wrench, i.e., the operator should be able to reliably ascertain when a certain torque is exceeded during the screwing in or out.

U.S. Pat. No. 5,337,638 describes a generic torque wrench wherein the jaw part remains in an overload position when an overload occurs. It must be pivoted out of this overload position back into an operational position by the operator. In certain working situations, this can disturb the operating sequence.

SUMMARY OF THE INVENTION

The object of the invention is to so design a generic surgical torque wrench that the operator can, on the one hand, reliably determine when a maximum torque is exceeded, but, on the other hand, is not prevented from continuing to work after such a snapping-out.

This object is accomplished in a surgical torque wrench of the kind described at the outset, in accordance with the invention, in that there is operative between handle part and jaw part a spring under whose action the jaw part pivots automatically from an overload position with released holding device back into the operational position in which the holding device is active. After a snapping-out the jaw part, therefore, pivots back automatically into the operational position again so the operation can be continued immediately.

It is expedient for there to be operative between jaw part and handle part a stop which enables pivoting of the jaw part relative to the handle part in one direction only when the holding device is released. The snapping-out, therefore, occurs in one direction only. In the opposite direction, on the other hand, the torque wrench can be used without snapping out, i.e., with an optionally high torque. This can be used, for example, for screwing in with a limited torque, but screwing out with an optionally high one. On the other hand, it is also possible to deliberately avoid the snapping-out of the torque wrench by turning round the torque wrench.

The pivot axis preferably lies between the jaw of the jaw part and the rear end of the jaw part, and the holding device engages the rear end of the jaw part. In particular, the pivot axis can be spaced at a considerably smaller distance from the jaw than from the rear end, for example, the ratio can be 1:5.

Provision is made in a preferred embodiment for the holding device to be a form-locking device with fixed release force. Here various possibilities are available to one skilled in the art. Of crucial importance in a form-locking device is the positive engagement of one shaped part in another shaped part, and this engagement has to be overcome by a fixed release force.

In a particularly preferred embodiment, provision is made for the holding device to comprise a spring-loaded detent member which is displaceable in the direction towards the pivot axis, engages a recess on the jaw part and is lifted out of the recess against the spring loading when a certain torque is exceeded.

Herein it is advantageous for the detent member to be mounted for longitudinal displacement in the handle part.

In particular, the detent member can be mounted on a guide body which is longitudinally displaceable in the handle part, and a spring supported on the handle part can engage the guide body.

In a preferred embodiment, provision is made for the handle part to comprise a cylindrical guide sleeve having a piston-shaped guide body mounted for longitudinal displacement therein and receiving a pressure spring.

In surgical torque wrenches of this kind, it is extremely important for the release forces of the holding device to maintain the initially set value. Such torque wrenches must be sterilized after use, and changes in the friction ratios could occur in the course of this, for example, owing to removal of a lubricant. This change in the friction ratios of, for example, the guide body and the detent member could bring about a change in the release forces.

In order to avoid this, in accordance with a preferred embodiment, provision may be made for the guide body and its guide to form a lubricant-free plastic-metal pairing. Such material pairing enables good sliding behavior with reproducible friction values which can also not be changed by the sterilizing operations.

In particular, the guide body may consist of polyetherketone, and the guide of stainless steel. This plastic material and stainless steel constitute an ideal slide pairing and are excellent for sterilization.

It is also expedient for the guide body to be secured in the guide sleeve against rotation about the longitudinal axis of the guide sleeve, for example, by pins mounted on the guide sleeve and engaging guide slots on the guide body.

In principle, it is possible to use a holding device with a release value which is always identical. However, it is expedient for the spring loading of the detent member to be adjustable so the release force of the torque wrench can thereby be adjusted.

In particular, provision may be made for the support of the spring to be adjustable for adjustment of the spring loading.

In an embodiment with a guide sleeve, it is advantageous for the guide sleeve to have a closure plug on which there is arranged an adjustable spacer for a pressure spring support.

This spacer can be an adjusting screw which rests against a pressure plate which is longitudinally displaceable in the guide sleeve.

In particular, the adjusting screw can be countersunk in a threaded bore of the closure plug, and it is then advantageous for the threaded bore to be closed by a plug inserted therein. Therefore, the adjusting screw can only be adjusted when the plug is removed. In operation, however, this plug is used so that unintentional adjustment of the adjusting screw and thus unintentional adjustment of the spring loading are excluded. This plug can be a threaded plug.

It is expedient for the guide sleeve to have side openings, for example, in the form of elongate windows. This makes it possible to also reliably reach the interior of the guide sleeve during the sterilization.

To avoid penetration of body fluids, etc. into the guide sleeve during operation, and to obtain good gripping characteristics, provision may be made for a handle sleeve which is releasably connected to the guide sleeve to be pushed over the guide sleeve.

The handle sleeve is preferably screwed onto the guide sleeve.

It can cover the guide sleeve and a closure plug inserted therein when it is pushed completely onto the guide sleeve.

In accordance with a preferred embodiment, provision is made for the handle sleeve, in its position in which it is completely pushed onto the guide sleeve, to form the stop for the handle part which enables pivoting of the jaw part relative to the handle part in one direction only when the holding device is released. The handle sleeve thus prevents the jaw part from being pivotable relative to the handle part in both directions. A snapping-out is only possible in one direction. In the other direction the screwed-on handle sleeve holds the jaw part in the operational position and thus makes it possible for optionally high torques to be applied in one direction of rotation.

In accordance with a preferred embodiment, provision is made for the detent member to be a roller which is rotatable parallel to the pivot axis of the jaw part, in particular, this roller is a ball bearing. In this way, one obtains precisely defined friction values between detent member and jaw part, and this is important for the reproducibility of the release forces.

In particular, provision may be made for the roller to be a packed ball bearing which is filled with a sterilizable grease. This also contributes to the instrument being perfectly sterilizable, but to the friction values not being changed during the sterilization.

It is expedient for the recess on the jaw part to be an arcuate recess in a rear end edge of the jaw part.

This end edge can be inclined slightly in relation to a tangent to a circle drawn around the pivot axis of the jaw part, for example, at an angle of between 5 and 10°. This results in the lifting of the detent member out of the recess being difficult in one direction and easily possible in the other direction. In the difficult direction, the detent member is lifted out upon snapping-out of the torque wrench when a certain torque is exceeded. A lifting out of the detent member to the easy side occurs when the jaw part is exchanged. Also, owing to the inclined arrangement of the end edge, the detent member, after rising out of the arcuate recess, pivots the end edge still further by engaging it, i.e., after passing a dead center, the detent member reinforces the pivoting-out of the jaw part on rising out of the recess so the exchange of the jaw part is additionally facilitated.

It is expedient for the handle part to have two parallel arms between which the jaw part is received, and for the pivot axis of the jaw part to be arranged at the front end of the arms.

In a preferred embodiment, a web joining the two arms can form the stop which limits the pivot angle of the jaw part relative to the handle part when the holding device is released.

In a preferred embodiment, provision is made for the pivot bearing of the jaw part to be releasable on the handle part. This makes it possible for the jaw part to be exchanged relative to the handle part, for example, in order to use a jaw part with a differently dimensioned jaw, or for the purpose of sterilization after use.

In particular, provision may be made for a bearing shaft to be axially displaceably arranged on the handle part between a bearing position in which it extends through a bearing opening of the jaw part and a release position in which it is pulled out of the bearing opening.

It is expedient for the bearing shaft to be undetachably held on the handle part.

In order to achieve this, there may be arranged on the handle part a projection which engages in a longitudinal groove of the bearing shaft.

It is advantageous for the longitudinal groove of the bearing shaft to have an end region bending round in the circumferential direction and extending at an incline to the longitudinal direction of the bearing shaft, and for a turning grip to be arranged on the bearing shaft. Owing to this configuration of the longitudinal groove, a rotation of the bearing shaft about its longitudinal axis automatically also results in an axial displacement so that the bearing shaft can be moved between release position and bearing position by turning the turning grip.

Provision is made in a preferred embodiment for there to be arranged in the longitudinal groove at the end of the inclined end region of the longitudinal groove a recess extending in the longitudinal direction of the bearing shaft and receiving the projection on the handle part in the bearing position of the bearing shaft, and for the bearing shaft to be resiliently pressed against the projection on the handle part in the bearing position.

This results in a bayonet-type locking of the bearing shaft in the bearing position. The projection on the handle part can only be lifted out of the recess when the bearing shaft is axially displaced against the action of a spring, i.e., for rotation of the bearing shaft and thus for axial displacement it is necessary beforehand to press in the bearing shaft axially beyond the bearing position.

It is expedient for there to be mounted in the bearing shaft a pressure member which protrudes from the end face of the bearing shaft and is resiliently pressable into the bearing shaft. The pressure member is preferably in the form of a ball. When the bearing shaft is pushed into the bearing position, this pressure member rests against the handle part and generates the spring force with which the bearing shaft is pushed against the projection on the jaw part, which thus enables the bayonet-type locking.

In addition, it is advantageous for the pressure member to project into the insertion space of the jaw part in the release position of the bearing shaft. This results, even when the bearing shaft is pushed into the release position, in still a slight support for the jaw part, as the pressure member still projects slightly into the bearing opening of the jaw part. To remove the jaw part, the pressure member must be pushed resiliently into the bearing shaft, i.e., a certain force is necessary to remove the jaw part from and insert the jaw part into the bearing position. On the one hand, this prevents the jaw part from falling unintentionally out of the handle part when the bearing shaft is moved into the release position. On the other hand, it indicates clearly to the operator on inserting the jaw part that the jaw part is correctly positioned and that in this position the bearing shaft can be pushed fully into the bearing opening.

The following description of preferred embodiments of the invention serves in conjunction with the drawings the purpose of further explanation.

BRIEF DESCRIPTION OF THE DRAWINGS

FIG. 7 a plan view of the pivot bearing area of the jaw part on the grip part with inserted jaw part and with the bearing shaft in bearing position;

FIG. 8 a view similar to FIG. 7 without jaw part with the bearing shaft in release position;

FIG. 9 a side view of the bearing area of FIGS. 7 and 8 with the bearing shaft in bearing position (unbroken lines) and in release position (dot-and-dash lines); and FIG. 10 a sectional view along line 10—10 in FIG. 7.

DETAILED DESCRIPTION OF THE INVENTION

Figure 1:
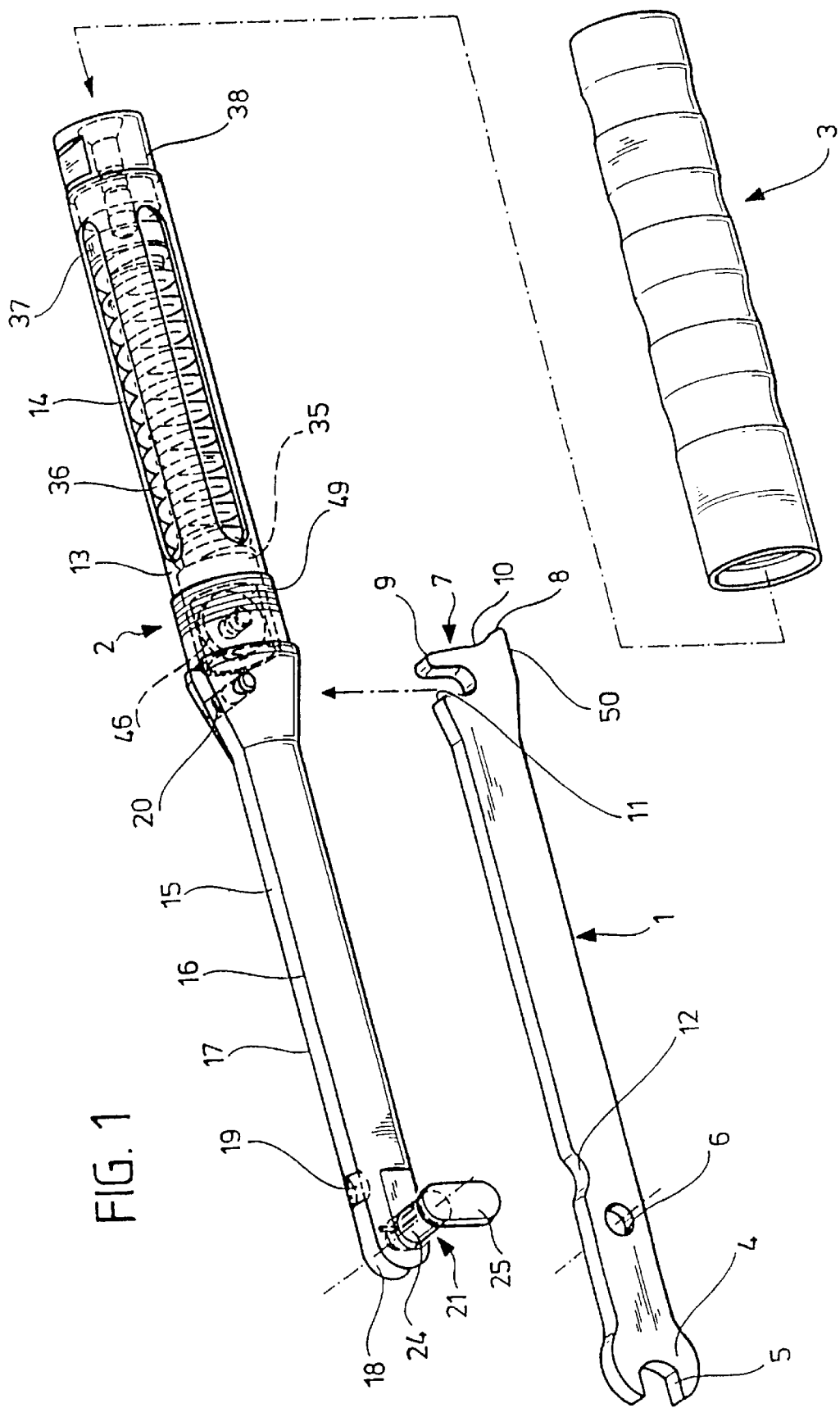
FIG. 1 a perspective view of a surgical torque wrench in the disassembled state.
Figure 2:
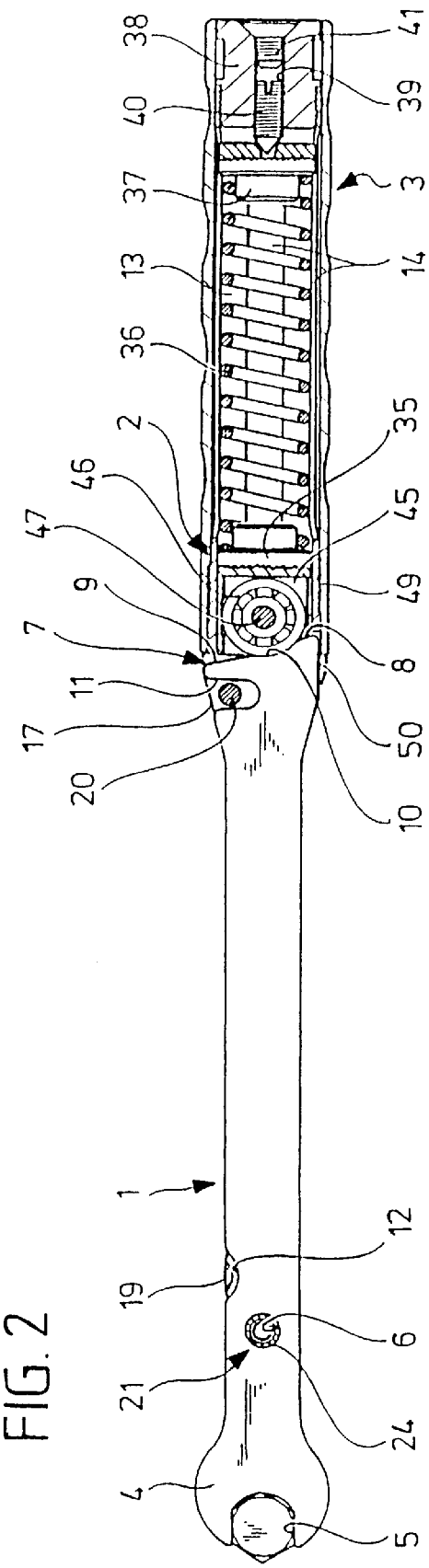
FIG. 2 a longitudinal sectional view of the assembled torque wrench of FIG. 1 in operational position.
Figure 3:
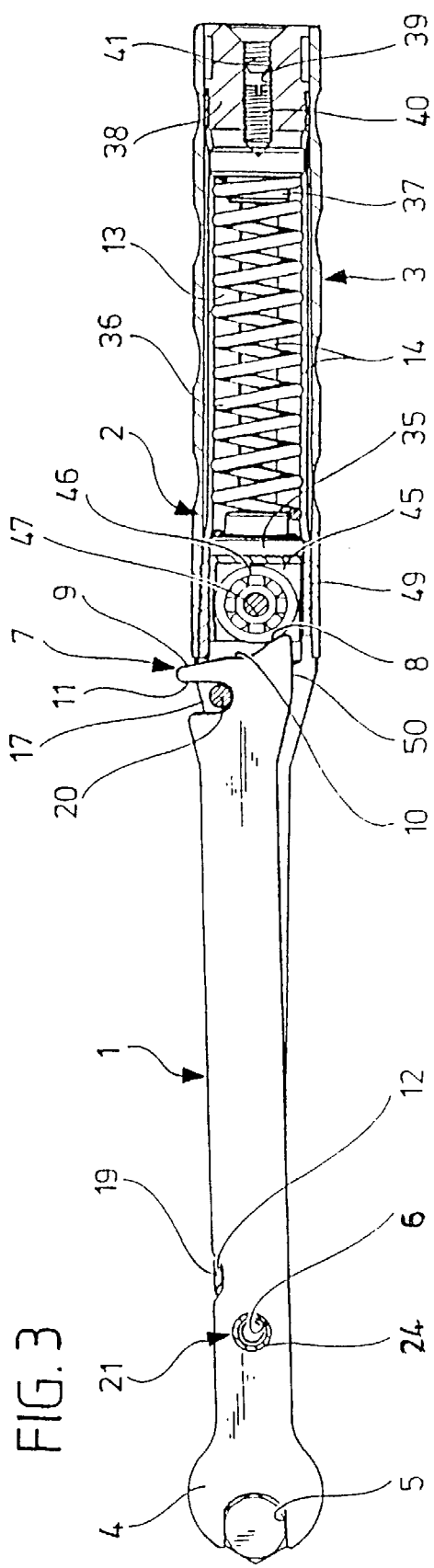
FIG. 3 a view similar to FIG. 2 in the snapped-out position.
Figure 4:
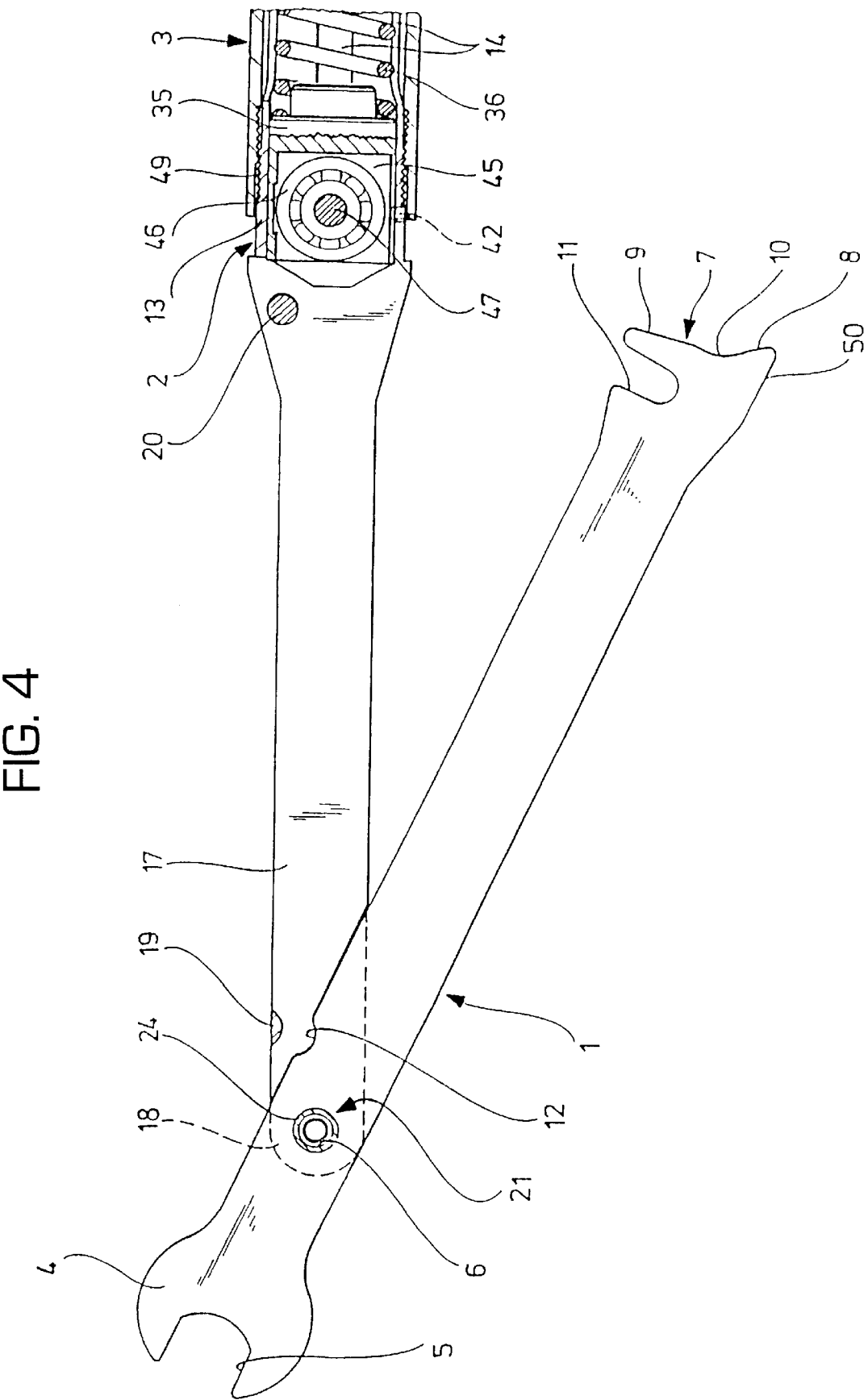
FIG. 4 a longitudinal sectional view of the front part of the torque wrench of FIG. 1 with the jaw part pivoted out for exchange.

The surgical torque wrench shown in the drawings comprises essentially three parts, namely a jaw part 1, a handle part 2 and a handle sleeve 3.

The jaw part 1 has the shape of a conventional wrench, i.e., the jaw part 1 has the shape of a flat, plate-shaped band which at the front end has a widened jaw area 4 with a four-edge jaw 5 which can be rotationally fixedly applied to a hexagonal nut or a hexagonal head of a screw. Arranged at some distance to the side of the jaw 5 in the jaw part 1 is a bearing opening 6 which extends through the jaw part.

The distance of the bearing opening 6 from the jaw 5 is considerably smaller than the distance of the bearing opening 6 from the rear end edge 7 of the jaw part 1, for example, the ratio may be 1:5.

This rear end edge 7 extends essentially transversely to the longitudinal direction of the jaw part 1 and includes three areas which are separate from one another. A first straight-lined area 8 adjoining the bottom edge of the jaw part 1 is inclined in relation to the longitudinal direction of the jaw part 1 about an angle of approximately 70 to 75° in the direction towards the jaw area 4. A likewise straight-lined area 9 adjoining the top edge of the jaw part 1 has a somewhat larger inclination in relation to the longitudinal direction of the jaw part, for example, of the order of magnitude of 80°. An arcuate recess 10 is arranged between the straight-lined areas 8 and 9.

Provided immediately adjacent to the end edge 7 in the jaw part 1 is an elongate cut-out 11 starting from the top edge of the jaw part 1, extending transversely to the longitudinal direction of the jaw part 1 and reaching almost as far as the center of the jaw part 1.

Finally, in the area of the bearing opening 6 there is arranged in the top edge of the jaw part 1 an arcuate cut-out 12 of low depth.

The handle part 2 comprises an elongate, tubular guide sleeve 13 with elongate, window-type openings 14, which carries at its front end two parallel arms 16 and 17 extending in the longitudinal direction of the guide sleeve 13 and forming between them a space 15. The arms 16 and 17 are joined together in the region of their front end 18 by a web 19 formed on the top side of the arms 16 and 17 and in the region of transition to the guide sleeve 13 by a transverse pin 20.

In the region of the front end 18, the two arms 16 and 17 form a pivot bearing 21 for the jaw part 1. For this purpose, there is arranged in an arm 16 a transverse bore 22 leading into the space 15, and in the other arm 17 a blind-hole bore 23 aligned with the transverse bore 22 and opening towards the space 15.

Longitudinally displaceably and rotatably received in the transverse bore 22 is a bearing shaft 24 which carries a radially projecting turning grip 25 at its end protruding outwards from the transverse bore 22. Machined in the outer circumference of the bearing shaft 24 is an axially parallel longitudinal groove 26 which bends round in the circumferential direction at its end adjacent to the turning grip 25 and extends there at an incline to the longitudinal axis of the bearing shaft (FIG. 8). At the end of this inclined part 27 of the longitudinal groove 26 which extends over a circumferential angle of approximately 90°, the longitudinal groove 26 has a recess 28 extending in the axial direction, and this recess 28 turns back in the direction towards the end of the bearing shaft 24 facing away from the turning grip 25 (FIG. 7).

Projecting into the longitudinal groove 26 is a pin 29 which is attached to the arm 16 and protrudes radially into the transverse bore 22. On the one hand, the projecting of the pin 29 into the longitudinal groove 26 ensures that the bearing shaft 24 is undetachably guided in the transverse bore 22, on the other hand, rotation of the bearing shaft 24 with the aid of the turning grip 25 results in an axial displacement of the bearing shaft 24 when the pin 29 is located in the inclined region 27.

Displaceably mounted in the bearing shaft 24 in a blind hole bore 30 is a ball 31 which protrudes through an opening 32 in the end face 33 of the bearing shaft 24 but which is undetachably held in the blind hole bore 30. The ball 31 is pushed out of the blind hole bore 30 by a pressure spring 34 arranged in the blind hole bore 30 and supported, on the one hand, on the ball 31, and, on the other hand, on the bearing shaft 24.

The bearing shaft 24 is displaceable between two end positions at the transverse bore 22. The one end position is the bearing position. In this bearing position, the bearing shaft 24 is pushed to a maximum extent into the transverse bore 22. It then projects into the blind hole bore 23 and is resiliently supported by means of the ball 31 at the bottom of the blind hole bore 23. In this bearing position, the pin 29 projects into the recess 28 at the end of the inclined region 27 of the longitudinal groove 26 and is held by the resilient displacement of the bearing shaft 24 in this recess 28. A kind of bayonet locking of the bearing shaft 24 in the bearing position is thus achieved.

In order to release this position, the bearing shaft 24 must be turned with the aid of the turning grip 25. The pin 29 then exits from the recess 28, but to do so, must displace the bearing shaft 24 slightly against the force of the pressure spring 34, i.e., turning of the bearing shaft out of the bearing position requires a certain minimum force so that unintentional turning is excluded.

In the other end position of the bearing shaft 24, the so-called release position, the bearing shaft 24 is pulled out of the transverse bore so far that the pin 29 strikes the end opposite the inclined end of the longitudinal groove 26 (FIG. 8). The ball 31 of the bearing shaft 24 then still protrudes slightly into the space 15 (FIG. 8).

In this release position, the jaw part 1 can be inserted into the space 15 between the two arms 16 and 17 in such a way that the bearing opening 6 is aligned with the transverse bore 22 and the blind hole bore 23. As the ball 31 projects slightly into the space 15, the user must apply a certain force with the jaw part 1 when inserting the jaw part 1 into the space 15, in order to push the ball 31 into the blind hole bore 30 against the force of the pressure spring 34. Once the bearing opening 6 is in alignment with the transverse bore 22 and the blind hole bore 23, the ball 31 moves forwards elastically under the effect of the pressure spring 34 and engages slightly in the bearing opening 6. In this way, when inserting the jaw part 1, the user feels the correct positioning of the bearing opening 6 in alignment with the transverse bore 22 and the blind hole bore 23 by the forward movement of the ball 31 and can then push the bearing shaft 24 forwards in the transverse bore 22. The bearing shaft extends through the bearing opening 6 in the jaw part 1 and finally enters the blind hole bore 23. By turning the turning grip 25, the bearing shaft 24 is pushed forwards into the bearing position and locked in the described manner by engagement of the pin 29 in the recess 28. In this way, the jaw part 1 is pivotably mounted between the arms 16 and 17. Release of the jaw part 1 is possible in the reverse manner by the bearing shaft 24 being turned through 90° by means of the turning grip 25 and then pulled out of the transverse bore 22.

Longitudinally displaceably mounted in the guide sleeve 13 is a piston 35 on which a helical spring 36 is supported. Adjacent to the piston 35 the helical spring is arranged in the guide sleeve 13, and its opposite end rests against a pressure plate 37 likewise mounted for longitudinal displacement in the guide sleeve 13. On the side opposite the arms 16 and 17, the guide sleeve 13 is closed off by a screwed-in closure plug 38 which has a central, longitudinally extending threaded bore 39. Screwed into the threaded bore 39 is a headless adjusting screw 40 which rests against the pressure plate 37 and, therefore, determines the distance of the pressure plate 37 from the closure plug 38 in accordance with the respective screw-in depth. The threaded bore 39 is closed by a threaded plug 41 which is screwed into the part of the threaded bore 39 remaining free.

Figure 6:
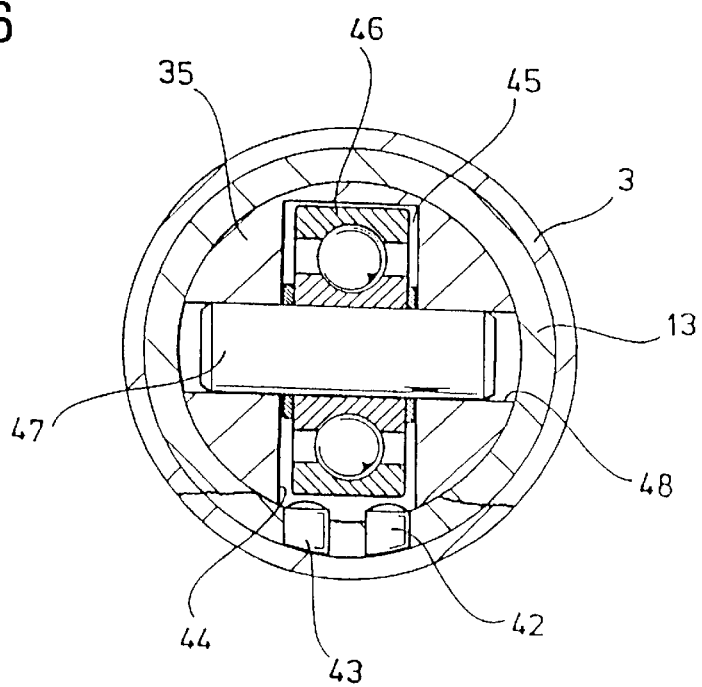
FIG. 6 a sectional view along line 6—6 in FIG. 5.

The piston 35 is secured in the guide sleeve 13 against rotation about the longitudinal axis of the guide sleeve 13 by two pins 42, 43 which project into a longitudinal slot 44 of the piston 35 being arranged on the guide sleeve (FIG. 6).

Arranged in the piston 35 is a chamber 45 which is open towards the arms 16, 17. A ball bearing 46 is mounted in this chamber 45 for rotation about an axis of rotation extending transversely to the longitudinal axis of the guide sleeve 13 with the aid of a bearing shaft 47 which is arranged in a transverse bore 48 of the piston 35 (FIG. 6).

When a jaw part 1 is inserted between the arms 16 and 17, it is pivoted, after the pivot bearing 21 is produced in the described manner, such that the jaw part 1 engages completely in the space 15, i.e., the jaw part 1 is aligned parallel to the arms 16 and 17. On pivoting the jaw part 1 into this position, the straight-lined area 9 of the end edge 7 first comes to rest against the ball bearing 46 and displaces it together with the piston 35 accommodating it against the force of the pressure spring 36 slightly in the guide sleeve 13 until the ball bearing 46 snaps into the arcuate recess 10 in the end edge 7, and the piston 35 is pushed out of the guide sleeve 13 again under the action of the pressure spring 36. In this position, in which the ball bearing 46 engages the recess 10 of the end edge 7, the jaw part 1 is located in the operational position and is then also held therein by the engagement of the ball bearing 46 in the recess 10, i.e., the pivot angle of the jaw part 1 in relation to the handle part 2 is fixed in this way.

Figure 5:
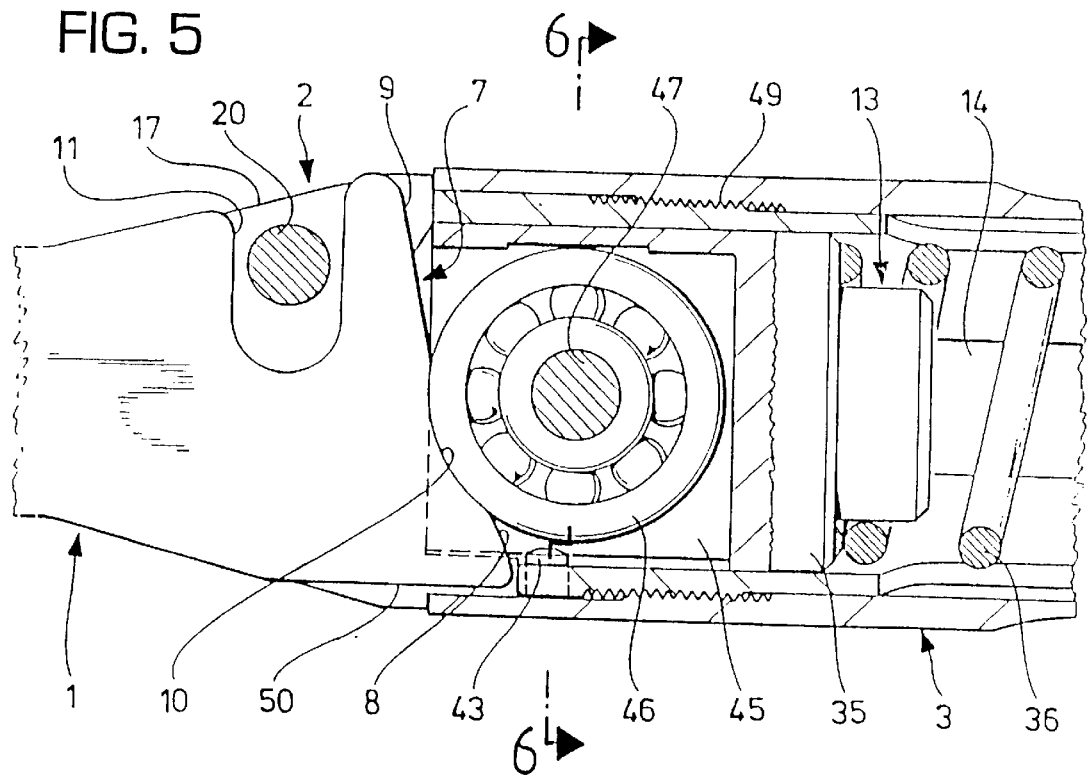
FIG. 5 an enlarged longitudinal sectional view of the holding device of the jaw part in operational position.

In this operational position of the jaw part 1, the handle sleeve 3 can be pushed from the rear side over the guide sleeve 13 of the handle part 2 and screwed onto an outer thread 49 of the guide sleeve 13. Once the handle sleeve 3 has been fully screwed onto the outer thread 49, it embraces the bottom edge 50 of the jaw part 1 at a slight distance therefrom (FIG. 5) so that pivoting of the jaw part 1 in one direction is prevented, namely in the direction in which the jaw part 1 has previously been pivoted into the operational position.

In the described position, in which the ball bearing 46 engages in the recess 10 of the end edge 7 of the jaw part 1, and in which the handle sleeve 3 is completely screwed onto the outer thread 49, the described instrument is ready for operation. Turning of the instrument in a first direction, in the clockwise direction in the drawings, results in a rotationally fixed connection between jaw part 1 and handle part 2 so long as the ball bearing 46 engages the recess 10. As the jaw part 1 is pivotably mounted on the handle part 2, upon applying a torque, a force which attempts to lift the ball bearing 46 out of the recess is exerted from the end edge 7 on the ball bearing 46 and thus on the piston 35 receiving the ball bearing 46. This is counteracted by the force of the pressure spring 36 which presses the ball bearing 46 into the recess 10.

In the case of low torques, the force of the spring 36 is adequate to hold the ball bearing 46 in the recess 10. A rotationally fixed connection between jaw part 1 and handle part 2 is, therefore, maintained.

However, when a certain torque is reached, the pressure spring 36 can no longer hold the ball bearing 46 in the recess 10. The ball bearing 46 is lifted out of the recess 10 against the force of the pressure spring 36, and, therefore, the rotationally fixed connection between jaw part 1 and handle part 2 is released. The Jaw part 1 then pivots about the pivot bearing 21, i.e., the jaw part 1 snaps out sideways relative to the handle part 2. This snap-out movement is limited by the transverse pin 20 which engages the cut-out 11 striking the edge of the cut-out 11. In this snapped-out position, the operator can, therefore, continue the screwing movement, namely with a higher torque. However, he will readily notice the snapping-out of the instrument and, therefore, the exceeding of the maximum torque, and so this is an indication to him that the torque now applied in the snapped-out state exceeds a threshold value.

When the ball bearing 46 is lifted out of the recess 10, it lies against the straight-lined area 8 of the end edge 7 and owing to the force of the spring 36 exerts a returning force on the jaw part 1 by means of which the jaw part 1 is pivoted back into the operational position again, in which the ball bearing 46 can engage in the recess 10 again. If the operator stops the screwing-in movement when the instrument snaps out, the instrument, therefore, automatically moves into the operational position again, but if he continues the screwing-in movement, the instrument remains in the snapped-out state and thereby indicates to the operator that the maximum value of the torque is exceeded.

On turning the instrument in the opposite direction, no such snapping-out movement can occur as the jaw part 1 is prevented from a snapping-out movement by the handle sleeve 3. The handle sleeve 3 thus acts as stop which enables a snapping-out of the jaw part 1 in one direction only.

The handle sleeve also prevents removal of the jaw part 1 from the handle part 2 as removal of the jaw part 1 requires pivoting in the direction opposite to the snapping-out direction in order to move the transverse pin 20 out of the cut-out 11 of the jaw part 1. Therefore, when a jaw part 1 has to be exchanged, the operator must first screw the handle sleeve 3 back on the outer thread 49 until the bottom edge 50 of the jaw part 1 is released. The handle sleeve can, however, remain on the guide sleeve 13 as the outer thread 49 has a sufficient height.

Only after this pivoting-out of the jaw part 1 is the pivot bearing 21 released in the described manner so that, if required, a new jaw part can then be inserted.

To clean the described instrument, it is completely disassembled in the described manner, namely into jaw part 1, handle part 2 and handle sleeve 3, which are then sterilized separately. All parts are freely accessible and so thorough cleaning and sterilization can be carried out.

What is claimed is:

1. A surgical torque wrench, comprising:
   (a) a jaw part adapted for application to an element to be turned;
   (b) a handle part adjoining said jaw part for turning said jaw part; wherein:
      said jaw part is joined to said handle part, and is pivotable with respect to said handle part about a pivot axis from an operative position to an overload position when a torque exceeding a predetermined torque is exerted on said handle part; and
      said pivot axis extends parallel to an axis of rotation of the element to be turned;
   (c) a spring;
   (d) a holding device provided between the jaw part and the handle part; wherein:
      said holding device is biased by said spring for fixing said jaw part in said operative position at a first angular position relative to said handle part when a torque less than the predetermined torque is exerted on said handle part;
      said holding device is releasable to allow said jaw part to pivot from said operative position into said overload position at a second angular position relative to said handle part when a torque exceeding the predetermined torque is exerted on said handle part; and
      once said jaw part has entered said overload position, said spring biases said holding device to bias said jaw part back into said operative position; and
   (e) a locking element movable with respect to said handle part between first and second positions; wherein:
      in said first position, said locking element embraces a portion of said jaw part to prevent removal of said jaw part from said handle part; and
      in said second position, said locking element releases said portion of said jaw part to allow said jaw part to pivot from said operational position in a direction away from said overload position to facilitate removal of said jaw part from said handle part.

2. The surgical torque wrench of claim 1, wherein:
   said locking element comprises a handle sleeve surrounding said handle part, at least in part, and adapted to be secured thereto at said first and second positions along a longitudinal axis of said handle part.

3. The surgical torque wrench of claim 2, wherein:
   in said first position, handle sleeve enables pivoting of said jaw part relative to said handle part in one direction only.

4. The surgical torque wrench of claim 2, wherein:
   said handle part comprises a cylindrical guide sleeve having a piston-shaped guide body mounted for longitudinal displacement therein and receiving said spring; and
   said handle sleeve is pushable over said guide sleeve and is releasably connectable to said guide sleeve.

5. The surgical torque wrench of claim 4, wherein:
   said handle sleeve is adapted to threadedly engage said guide sleeve in said first and second positions.

6. The surgical torque wrench of claim 4, wherein:
   said handle sleeve covers said guide sleeve and a closure plug inserted therein.

7. The surgical torque wrench of claim 4, wherein:
   in said first position, said handle sleeve is completely pushed onto said guide sleeve, and forms a stop for said jaw part which enables pivoting of said jaw part relative to said handle part in one direction only from said operative position.

8. The surgical torque wrench of claim 2, wherein:
   said second position is rearward of said first position on said handle part.

9. The surgical torque wrench of claim 1, wherein:
   said pivot axis is arranged between a jaw of said jaw part and a rear end of said jaw part; and
   said holding device engages said rear end of said jaw part.

10. The surgical torque wrench of claim 9, wherein:
   said pivot axis is spaced at a considerably smaller distance from said jaw than from said rear end.

11. The surgical torque wrench of claim 1, wherein:
   said handle part comprises two parallel arms, between which said jaw part is received; and
   said pivot axis of said jaw part is arranged at a front end of said parallel arms.

12. The surgical torque wrench of claim 11, further comprising:
   a web joining said two arms; wherein:
      said web forms a stop that limits a pivot angle of said jaw part relative to said handle part when said holding device is released.

13. The surgical torque wrench of claim 1, wherein:
   said holding device is a form-locking device with a fixed release force.

14. The surgical torque wrench of claim 13, wherein:
   said holding device comprises a spring-loaded detent member which is displaceable in a direction towards said pivot axis, and which engages a recess on said jaw part and is lifted out of said recess against a bias of said spring when a torque exceeding said predetermined torque is applied to said handle part.

15. The surgical torque wrench of claim 14, wherein:
   said recess on said jaw part is an arcuate recess in a rear end edge of said jaw part.

16. The surgical torque wrench of claim 15, wherein:
   said rear end edge is inclined slightly in relation to a tangent to a circle drawn about said pivot axis of said jaw part.

17. The surgical torque wrench of claim 14, wherein:
   said detent member comprises a roller which is rotatable parallel to said pivot axis of said jaw part.

18. The surgical torque wrench of claim 17, wherein:

said roller comprises a ball bearing.

19. The surgical torque wrench of claim 17, wherein:

said roller comprises a packed ball bearing which is filled with a sterilizable grease.

20. The surgical torque wrench of claim 14, wherein:

the spring loading of said detent member is adjustable.

21. The surgical torque wrench of claim 20, further comprising:

an adjustable support for said spring for providing adjustment of said spring loading.

22. The surgical torque wrench of claim 14, wherein:

said detent member is mounted for longitudinal displacement in said handle part.

23. The surgical torque wrench of claim 22, further comprising:

a guide body which is longitudinally displaceable in said handle part; wherein:
said detent member is mounted in said guide body; and
said spring is supported on said handle part and engages said guide body.

24. The surgical torque wrench of claim 23, wherein:

said handle part comprises a cylindrical guide sleeve having a piston-shaped guide body mounted for longitudinal displacement therein and receiving said spring.

25. The surgical torque wrench of claim 24, wherein:

said guide body and said guide sleeve form a lubricant-free plastic-metal pairing.

26. The surgical torque wrench of claim 25, wherein:

said guide body comprises polyetherketone and said guide sleeve comprises stainless steel.

27. The surgical torque wrench of claim 24, wherein:

said guide body is secured in said guide sleeve against rotation about a longitudinal axis of said guide sleeve.

28. The surgical torque wrench of claim 24, wherein:

said guide sleeve has side openings to facilitate sterilization of an interior of said guide sleeve.

29. The surgical torque wrench of claim 24, wherein:

said guide sleeve has a closure plug on which there is arranged an adjustable spacer for a pressure spring support.

30. The surgical torque wrench of claim 29, wherein:

said adjustable spacer comprises an adjusting screw which rests against a pressure plate which is longitudinally displaceable in said guide sleeve.

31. The surgical torque wrench of claim 30, wherein:

said adjusting screw is countersunk in a threaded bore of said closure plug; and said threaded bore is closed by a plug inserted therein.

32. The surgical torque wrench of claim 31, wherein:

said plug inserted in said threaded bore is a threaded plug.

33. The surgical torque wrench of claim 1, wherein:

a pivot bearing of said jaw part is releasable on said handle part.

34. The surgical torque wrench of claim 33, further comprising:

a bearing shaft that is axially displaceably arranged on said handle part between a bearing position in which it extends through a bearing opening of said jaw part, and a release position, in which it is pulled out of said bearing opening.

35. The surgical torque wrench of claim 34, wherein:

said bearing shaft is undetachably held on said handle part.

36. The surgical torque wrench of claim 35, wherein:

a projection is arranged on said handle part; and said projection engages in a longitudinal groove of said bearing shaft.

37. The surgical torque wrench of claim 36, wherein:

said longitudinal groove of said bearing shaft has an end region bending around in a circumferential direction and extending at an incline to the longitudinal axis of said bearing shaft; and a turning grip is arranged on said bearing shaft.

38. The surgical torque wrench of claim 37, wherein:

a recess is arranged in said longitudinal groove at an end of said inclined end region of said longitudinal groove;

said recess extends in the longitudinal direction of said bearing shaft and receives said projection on said handle part in said bearing position of said bearing shaft; and in said bearing position, said bearing shaft is resiliently pressed against said projection on said handle part.

39. The surgical torque wrench of claim 38, further comprising:

a pressure member mounted in said bearing shaft that protrudes from an end face of said bearing shaft and is resiliently pressable into said bearing shaft.

40. The surgical torque wrench of claim 39, wherein:

said pressure member is a ball.

41. The surgical torque wrench of claim 39, wherein:

said pressure member projects into an insertion space of said jaw part in the release position of said bearing shaft.

* * * * *

UNITED STATES PATENT AND TRADEMARK OFFICE
CERTIFICATE OF CORRECTION

PATENT NO. : 6,021,694
DATED : Feb. 8, 2000
INVENTOR(S) : Jens Beger

It is certified that error appears in the above-identified patent and that said Letters Patent is hereby corrected as shown below:

On the Title Page:

[73] Assignee: Aesculap AG & Co. KG

Signed and Sealed this

Third Day of April, 2001

Attest:

NICHOLAS P. GODICI

*Attesting Officer*   *Acting Director of the United States Patent and Trademark Office*